US008551986B2

(12) United States Patent
Elman et al.

(10) Patent No.: US 8,551,986 B2
(45) Date of Patent: Oct. 8, 2013

(54) TREATMENT OF SEQUELAE OF PSYCHIATRIC DISORDERS

(75) Inventors: Igor Elman, Ashland, MA (US); David Borsook, Concord, MA (US); Jan Wasley, Guilford, CT (US)

(73) Assignee: The McLean Hospital Corporation, Belmont, MA (US)

( * ) Notice: Subject to any disclaimer, the term of this patent is extended or adjusted under 35 U.S.C. 154(b) by 994 days.

(21) Appl. No.: 12/096,428

(22) PCT Filed: Dec. 7, 2006

(86) PCT No.: PCT/US2006/046788
§ 371 (c)(1),
(2), (4) Date: Sep. 26, 2008

(87) PCT Pub. No.: WO2007/067714
PCT Pub. Date: Jun. 14, 2007

(65) Prior Publication Data
US 2009/0196824 A1    Aug. 6, 2009

Related U.S. Application Data

(60) Provisional application No. 60/748,471, filed on Dec. 8, 2005.

(51) Int. Cl.
 A61K 31/55    (2006.01)
 A61K 31/44    (2006.01)
 A61K 49/00    (2006.01)
 A01N 43/42    (2006.01)
(52) U.S. Cl.
 USPC ............. 514/220; 514/282; 514/300; 424/9.1
(58) Field of Classification Search
 USPC ..................... 514/220, 282, 300; 424/9.1
 See application file for complete search history.

(56) References Cited

U.S. PATENT DOCUMENTS

| | | | | |
|---|---|---|---|---|
| 5,228,875 | A * | 7/1993 | Swenson, Sr. | 439/784 |
| 5,512,593 | A | 4/1996 | Dante | |
| 5,945,416 | A * | 8/1999 | Shannon et al. | 514/220 |
| 6,020,310 | A * | 2/2000 | Beck et al. | 514/9.7 |
| 6,034,091 | A | 3/2000 | Dante | |
| 6,251,895 | B1 * | 6/2001 | Larsen et al. | 514/220 |
| 6,323,236 | B2 * | 11/2001 | McElroy | 514/439 |
| 6,375,957 | B1 | 4/2002 | Kaiko et al. | |
| 6,444,665 | B1 * | 9/2002 | Helton et al. | 514/220 |
| 6,680,310 | B2 | 1/2004 | Belanoff et al. | |
| 6,727,242 | B2 | 4/2004 | Radulovacki et al. | |
| 7,462,626 | B2 * | 12/2008 | Weber et al. | 514/282 |
| 2003/0170288 | A1 * | 9/2003 | Carr et al. | 424/426 |
| 2003/0191147 | A1 * | 10/2003 | Sherman et al. | 514/282 |
| 2004/0058910 | A1 | 3/2004 | Brown | |

FOREIGN PATENT DOCUMENTS

WO    WO 2004/004660    1/2004

OTHER PUBLICATIONS http://www2.courses.vcu.edu/ptxed/phtx604/powerpoint/download/Bipolar%20Disordes.PDF. (2003) 4 pages.*
Zimmerman (J. Psychiatric Research 37 (2003) 193-220).*
Schreiber et al (Neuroscience Letters 228:25-28 (1997).*
Malhorta et al. (J. Clin Psychiatry (2002; 63sup 4):24-32.*
Garner et al. (The J. of Pharm and Experimental therapeutics 282: 1253-1261 (1997).*
Duggan et al (Cochrane Database Syst Rev Apr. 18, 2005;(2) CD001359).*
Evans et al. (Aust N Z J Psychiatry. Jun. 2005;39(6):479-86).*
Recant et al. Peptides. 1980 Winter;1(4):309-13.*
Gracious et al. Psychiatry 2005 [January] a.*
al'Absi et al., "Sex Differences in Pain and Hypothalamic-Pituitary-Adrenocortical Responses to Opioid Blockade," Psychosom. Med. 66:198-206, 2004.
Baghdadli et al., "Review of Psychopharmacological Treatments in Adolescents and Adults with Autistic Disorders," Encephale. 28:248-254, 2002. Abstract only.
Becerra et al., "Reward Circuitry Activation by Noxious Thermal Stimuli," Neuron 32:927-946, 2001.
Burns, "Ultra-Low-Dose Opioid Antagonists Enhance Opioid Analgesia While Reducing Tolerance, Dependence and Addictive Properties," Recent Develop. Pain Res. 115-136, 2005.
Cohen et al., "Naloxone Reduces Food Intake in Humans," Psychosom. Med. 47:132-138, 1985.
Davis et al., "Analgesia to Pain Stimuli in Schizophrenics and Its Reversal by Naltrexone," Psychiatry Res. 1:61-69, 1979.
Drewnowski et al., "Taste Responses and Preferences for Sweet High-Fat Foods: Evidence for Opioid Involvement," Physiol. Behav. 51:371-379, 1992.
Elman et al., "Food Intake and Reward Mechanisms in Patients with Schizophrenia: Implications for Metabolic Disturbances and Treatment with Second-Generation Antipsychotic Agents," Neuropsychopharmacology 31:2091-2120, 2006.
Evans, D.L., "Pain Insensitivity in Psychotic Patients," Am. J. Psychiatry 137:507-508, 1980.
Gitlin et al., "Assessment of Naltrexone in the Treatment of Schizophrenia," Psychopharmacology 74:51-53, 1981.
Green et al., "Treatment of Schizophrenia and Comorbid Substance Use Disorder," Curr. Drug Targets CNS Neurol. Disord. 1:129-139, 2002.
Henderson et al., "Glucose Metabolism in Patients with Schizophrenia Treated with Atypical Antipsychotic Agents: A Frequently Sampled Intravenous Glucose Tolerance Test and Minimal Model Analysis," Arch. Gen. Psychiatry 62:19-28, 2005.
Hollister, "Novel Drug Treatments for Schizophrenia," Psychopharmacol. Bull. 23:82-84, 1987.
Horrobin et al., "The Role of a Prostaglandin $E_1$ Deficiency in Schizophrenia: Interactions with Dopamine and Opiates," in Biochemistry of Schizophrenia and Addiction, pp. 3-17, 1979.
Hunsinger et al., "Is There a Basis for Novel Pharmacotherapy of Autism?" Life Sci. 67:1667-1682, 2000.
Kampov-Polevoy et al., "Sweet Liking and Family History of Alcoholism in Hospitalized Alcoholic and Non-Alcoholic Patients," Alcohol Alcohol. 36:165-170, 2001.
Kavanagh et al., "Substance Misuse in Patients with Schizophrenia," Drugs 62:743-755, 2002.

(Continued)

Primary Examiner — Shirley V Gembeh
(74) Attorney, Agent, or Firm — Clark & Elbing LLP

(57) ABSTRACT

In general, the invention provides methods and compositions for treating sequela of weight gain or pain insensitivity, e.g., in a subject suffering from a psychiatric disorder, such as schizophrenia. The combinations employed in the invention include a second generation antipsychotic agent and an opioid receptor antagonist.

17 Claims, No Drawings

(56) References Cited

OTHER PUBLICATIONS

Khojainova et al., "Olanzapine in the Management of Cancer Pain," *J. Pain Symptom Manage.* 23:346-350, 2002.

Kiser et al., "Olanzapine for the Treatment of Fibromyalgia Symptoms," *J. Pain Symptom Manage.* 22:704-708, 2001.

Malick et al., "A Comparison of Naloxone and Naltrexone in Laboratory Tests Predictive of Antipsychotic Potential," *Drug Develop. Res.* 3:253-259, 1983.

Malick et al., "Evaluation of Naloxone in Laboratory Tests Predictive of Clinical Antipsychotic Activity," *Comm. Psychopharmacol.* 1:475-488, 1977.

Marchesi et al., "Naltrexone Integrated Neuroleptic Treatment in Schizophrenia," *Biol. Psychiatry* 29(Suppl.):536, 1991.

Marchesi et al., "Naltrexone in Chronic Negative Schizophrenia," *Clin. Neuropharmacol.* 15(Suppl. 1, Pt. A):56A-57A, 1992.

Maruta, "Prescription Drug-Induced Organic Brain Syndrome," *Am. J. Psychiatry* 135:376-377, 1978.

Masand et al., "Metabolic and Endocrine Disturbances in Psychiatric Disorders: A Multidisciplinary Approach to Appropriate Atypical Antipsychotic Utilization," *CNS Spectr.* 10:suppl14 1-15, 2005.

Maxwell et al., "Naltrexone in the Treatment of Dually-Diagnosed Patients," *J. Addictive Diseases* 16:125, 1997.

Murthy et al., "Reduced Perception of Pain in Schizophrenia: Its Relevance to the Clinical Diagnosis of Compartment Syndrome," *Injury* 35:1192-1193, 2004.

Newcomer et al., "Abnormalities in Glucose Regulation During Antipsychotic Treatment of Schizophrenia," *Arch. Gen. Psychiatry* 59:337-345, 2002.

Petrakis et al., "Naltrexone Augmentation of Neuroleptic Treatment in Alcohol Abusing Patients with Schizophrenia," *Psychopharmacology* 172:291-297, 2004.

Rapaport et al., "Beneficial Effects of Nalmefene Augmentation in Neuroleptic-Stabilized Schizophrenic Patients," *Neuropsychopharmacology* 9:111-115, 1993.

Remington, "Schizophrenia, Antipsychotics, and the Metabolic Syndrome: Is There a Silver Lining," *Am. J. Psychiatry* 163:1132-1134, 2006.

Rodefer et al., "Naltrexone Pretreatment Decreases the Reinforcing Effectiveness of Ethanol and Saccharin but not PCP or Food Under Concurrent Progressive-Ration Schedules in Rhesus Monkeys," *Psychopharmacology (Berl)* 141:436-446, 1999.

Sernyak et al., "Naltrexone Augmentation of Neuroleptics in Schizophrenia," *J. Clin. Psychopharmacol.* 18:248-251, 1998.

Tsuang et al., "Treatment of Patients with Schizophrenia and Substance Abuse Disorders," *Curr. Pharm. Des.* 10:2249-2261, 2004. Abstract only.

Volavka et al., "Endorphins, Dopamine, and Schizophrenia," *Schizophr. Bull.* 5:227-239, 1979.

Wang et al., "Brain Dopamine and Obesity," *Lancet* 357:354-357, 2001.

Will et al., "Nucleus Accumbens Mu-Opioids Regulate Intake of a High-Fat Diet Via Activation of a Distributed Brain Network," *J. Neurosci.* 23:2882-2888, 2003.

International Search Report for PCT/US2006/046788, completed Oct. 12, 2007, mailed Nov. 14, 2007.

International Preliminary Report on Patentability for PCT/US2006/046788, issued Jun. 11, 2008.

Written Opinion of the International Searching Authority for PCT/US2006/046788, completed Oct. 12, 2007, mailed Nov. 14, 2007.

Kurbanov et al., "Effects of naltrexone on food intake and body weight gain in olanzapine-treated rats," *J. Psychopharmacol.* 26:1244-1251, 2012.

Tempel et al., "Neurochemical and functional correlates of naltrexone-induced opiate receptor up-regulation," *J. Pharamacol. Exp. Ther.* 232:439-444, 1985.

Langleben et al., "Depot naltrexone decreases rewarding properties of sugar in patients with opioid dependence," *Psychopharmacology* 220:559-564, 2012.

Timmerman, "Alkermes Aims for Psychiatric Drug That Won't Pack on the Pounds," http://www.xconomy.com/boston/2013/01/03/alkermes-aims-for-psychiatric-drug-that-wont-pack-on-the-pounds/?single_page=true, Jan. 3, 2013.

* cited by examiner

TREATMENT OF SEQUELAE OF PSYCHIATRIC DISORDERS

CROSS-REFERENCE TO RELATED APPLICATIONS

This application is the National Stage of International Application No. PCT/US2006/046788, filed Dec. 7, 2006, which claims benefit to U.S. Provisional Application No. 60/748,471, filed Dec. 8, 2005, hereby incorporated by reference.

BACKGROUND OF THE INVENTION

The invention relates to the field of treatment of sequelae of psychiatric disorders.

Obesity has reached pandemic proportions, and it is rapidly surpassing smoking as the number one killer in the industrialized world. Its annual cost to American society is staggering and is estimated to be around $117 billion due to related illnesses and loss of productivity.

In schizophrenia, obesity is twice as prevalent as in the general public, afflicting over half the patient population. Besides negative psychosocial impacts (e.g., distorted self-esteem and societal stigmatization) and medications noncompliance, schizophrenics appear to be particularly susceptible to the detrimental medical sequelae of obesity such as the Metabolic Syndrome or a cluster of cardiovascular risk factors, including abdominal adiposity, insulin resistance, impaired glucose tolerance, dyslipidaemia, and hypertension.

As documented in historical observations prior to the advent of antipsychotic agents, schizophrenia per se is associated with increased risk for obesity. The mechanisms of obesity in schizophrenia are not fully elucidated and could result from increased caloric intake, decreased energy expenditure owing to reduced physical activity, or a combination of both. Excessive caloric supply seems to play a major role, though, as schizophrenics tend to overconsume palatable 'junk' food, rich in sugar and saturated fat, that produces a substantial amount of body weight gain. These unhealthy eating habits ostensibly reflect illness' neuropathology, rather than patients' inability to afford healthier food choices, as they predict poor prognosis, including increased length of hospitalizations and deteriorated social functioning.

Administration of second generation antipsychotic agents (SGAs), such as clozapine, olanzapine, and to lesser degree quetiapine and risperidone, but not ziprasidone or aripiprazole, further worsens body weight gain problems mainly due to amplified and potentially insatiable appetite leading to increased consumption of the previously preferred diet.

Accordingly, there is a need for treatments of schizophrenia, and other psychiatric disorders, that reduce detrimental sequelae.

SUMMARY OF THE INVENTION

In general, the invention features the combination of second generation antipsychotic agents (SGAs) and opioid receptor antagonists and methods of their use. In one aspect, the invention provides a method of treating a sequela of weight gain or pain insensitivity in a subject, e.g., suffering from a psychiatric disorder, treated with a SGA by administering an opioid receptor antagonist to the subject in an amount sufficient to treat the sequela. In a related aspect, the invention provides a method of treating a psychiatric disorder by administering a SGA and an opioid receptor antagonist to a subject suffering from the psychiatric disorder in an amount sufficient to treat the psychiatric disorder, wherein the administration results in a reduction of a sequela of weight gain or pain insensitivity. The invention further provides a method of treating a sequela of weight gain or pain insensitivity in a subject suffering from a psychiatric disorder by administering a SGA and an opioid receptor antagonist to the subject in an amount sufficient to treat the sequela or pain insensitivity.

Treatment methods may also include a diagnosis of the particular disorder or condition by a physician or other medical professional prior to administration of the therapeutic regimen to the patient for treating the particular disorder or condition. Administration of the therapeutic compounds may also occur under the continuing care of a physician or medical professional.

The opioid receptor antagonist may be a μ, δ, or κ opioid receptor antagonist or a partial agonist, e.g., butorphanol, dezocine, nalbulphine, pentazocine, or buprenorphine. Exemplary opioid receptor antagonists include diprenorphine, naloxone, naltrexone, β-chlornaltrexamine, WIN44, 441-3, nalmefene, alvimopan (ADL 8-2698), methylnatrexone, cyprodime, naloxonazine, naloxazone, β-funaltrexamine, CTOP, naltrindole, ICI174,864, 7-benzylidenenaltrexone, naltriben, nor-binaltorphimine, 5'-guanidinonaltrindole, (−)-(1R,5R,9R)-5,9-diethyl-2-(3-furylmethyl)-2-hydroxy-6,7-benzomorphan (MR 2266), and a triethylenedioxy derivative of naltrexamine (TENA). Exemplary SGAs include sulpiride, amisulpride, clozapine, olanzapine, aripirazole, ziprasidone, quetiapine, risperidone, remoxipride, zotepine, sertindole, and iloperidone.

Exemplary psychiatric disorders include schizophrenia, autism, psychosis, schizoaffective disorder, mood disorders, anxiety disorders, dementia, sleep disorders, eating disorders, drug or alcohol abuse and dependence, impulse control disorders, personality disorders, and neuropathic pain. Sequelae of weight gain include weight gain, obesity, metabolic syndrome, insulin resistance, abdominal adiposity, impaired, glucose tolerance, dyslipidaemia, hypercholesterolemia, diabetes, and hypertension.

For opioid receptor antagonists, the dosage may range from 0.0001 to 1000 mg per day. In various embodiments, the opioid receptor antagonist is administered at less than 10 mg, 1 mg, 0.1 mg, 0.01 mg, or 0.001 mg per day. The ratio of opioid receptor antagonist to SGA may also be at most 1:1, 000. Other dosages are described herein.

The methods and combinations described herein may also be used in preventing a sequela of weight gain or pain insensitivity in a subject.

The invention also features a method of determining the efficacy of treatment with an SGA and an opioid receptor antagonist by determining the pain sensitivity of a subject having been administered an SGA and an opioid receptor antagonist. An increase in the level of pain sensitivity after administration of the SGA and opioid receptor antagonist is indicative of therapeutic efficacy.

The invention further features a method for determining a propensity for a subject to gain weight from SGA treatment by determining the pain sensitivity of the subject, wherein a decreased level of pain sensitivity compared to a healthy control is indicative of the propensity for the subject to gain weight from SGA treatment. If the subject has a decreased level of pain sensitivity, this method may further include administering an SGA and an opioid receptor antagonist in an amount effective to treat a sequela of weight gain.

In another aspect, the invention provides a pharmaceutical composition including (i) a second generation antipsychotic agent (SGA) and (ii) an opioid antagonist. The opioid antagonist is desirably present in an amount effective to reduce a sequela of weight gain or pain insensitivity, as described herein. The invention further features a kit including (i) a second generation antipsychotic agent (SGA), (ii) an opioid antagonist, and optionally (iii) instructions for administering the SGA and opioid antagonist to treat a psychiatric disorder while reducing a sequela of weight gain or pain insensitivity. In various kits and compositions, the opioid receptor antagonist may be present at less than 1 mg, 0.1 mg, 0.01 mg, or 0.001 mg. Moreover, the ratio of opioid receptor antagonist to SGA is preferably at most 1:1,000. In further embodiments, the SGA is present in a subtherapeutically effective amount. Other dosages are described herein.

In certain embodiments, the subject being treated does not suffer from co-morbid substance abuse or dependence, e.g., alcohol, opioid, or cocaine. In certain other embodiments, an opioid antagonist other than naltrexone or naloxone is employed to treat pain insensitivity or subjects suffering from co-morbid alcohol, opioid, or cocaine abuse or dependence. Combinations of two or more SGAs and/or opioid antagonists may also be employed in the methods and compositions described herein. Any of the SGAs described herein may be administered with any of the opioid receptor antagonists.

By "sequela of weight gain" is meant any medical condition that results from weight gain caused by a psychiatric disorder, treatment of the disorder, or a combination thereof. Sequela of weight gain include, without limitation, weight gain, obesity, metabolic syndrome, insulin resistance, abdominal adiposity, impaired glucose tolerance, dyslipidaemia, hypercholesterolemia, diabetes, and hypertension.

By "second generation antipsychotic agent" or "SGA" is meant an antipsychotic agent other than chlorpromazine, droperidol, fluphenazine, haloperidol, loxapine, mesoridazine, molindone, perphenazine, pimozide, prochlorperazine, promazine, thioridazine, thiothixene, and trifluoperazine. In general, SGAs produce fewer extrapyramidal side effects than first generation antipsychotic agents.

By "opioid receptor antagonist" is meant an agent that decreases opioidergic function by any mechanism.

By "preventing" is meant medical management of a patient directed to prevention of a disease, pathological condition, or disorder.

By "treating" is meant the medical management of a patient with the intent that a cure or amelioration of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

By "subtherapeutically effective amount" is meant an amount of a compound or combination of compounds insufficient on its own to treat a disease, pathological condition, or disorder.

Obesity and related metabolic disturbances in schizophrenia constitute a major cause for the 12-18 years shortened life span of the patients afflicted with this illness (Masand et al, 2005). Thus, the methods described herein address an issue of substantial public health significance. Furthermore, the diagnostic methods of the invention may have important implications for the primary and secondary prevention of obesity in schizophrenia. For example, increased opioidergic drive may be used to screen patients at risk for the development of obesity. Those found to possess high vulnerability for the development of obesity due to schizophrenia-related alterations in reward function may be counseled to avoid excessive sweet and fat consumption (primary prevention), or targeted for early intervention even in the presence of mild weight problems (secondary prevention). These methods may also be useful for recognition and treatment of hazardous eating habits in patients with other disorders, including obesity (Wang et al, 2001), substance use disorders (Kampov-Polevoy et al, 2001), and major depression (Papakostas et al, 2005).

Other features and advantages will be apparent from the following description and the claims.

DETAILED DESCRIPTION OF THE INVENTION

The invention features methods and compositions for the treatment of schizophrenia, and other psychiatric disorders. The methods include administering a second generation antipsychotic (SGA) compound and an opioid receptor antagonist to treat the psychiatric disorder, where this administration desirably results in the treatment of a sequela from the disorder. We believe that such sequelae result from opioidergic activity and that antagonism of this opioidergic activity will treat the sequelae.

The invention further features methods for determining the efficacy, or likelihood of efficacy, of the treatment methods described herein. These methods are based on determination of pain sensitivity.

Schizophrenia and Obesity

Olanzapine (Zyprexa®) is one of the most commonly used second generation antipsychotic drugs (SGAs), and it is approved by the Food and Drug Administration (FDA) for the treatment of schizophrenia, acute mania, agitation in schizophrenia, and in bipolar disorder as well as for maintenance therapy in bipolar disorder. The superior therapeutic profile of this (and other) SGAs, is however, tarnished by serious morbidity and mortality stemming from SGA-induced obesity and from the associated Metabolic Syndrome. As obesity and its detrimental health consequences are highly prevalent even in medication-free patients, metabolic adverse effects of olanzapine are particularly conspicuous in this patient population (reviewed in Elman et al, 2006).

The mechanisms of obesity in schizophrenics are likely to be multifactorial and to involve both pharmacological and neuropathological facets (reviewed in Elman et al, 2006; Remington, 2006). Among central and peripheral factors underlying obesity, we believe that the opioid system plays a critical role. Opioids increase food consumption by promoting homeostatic anabolic processes (i.e., hunger and conservation of energy) and restraining the catabolic processes (i.e., satiety signals) via the hypothalamic orexigenic pathways (Schwartz and Porte, 2005). For example, orexigenic and anorexigenic neuropeptides such as orexin (Sweet et al, 2004) and the brain-derived neurotrophic factor (BDNF; Weickert et al, 2003; Angelucci et al, 2005) are boosted and suppressed, respectively, by the opioids. Moreover, opioids enhance food reward as pleasure and positive affective states produced by consumption of palatable food are mediated via μ-opioid neurotransmission within the scattered network of subcortical and brainstem nuclei (Tanda and Di Chiara, 1998; Saper et al, 2002; Berridge, 2003; Berridge and Robinson, 2003), including the nucleus accumbens, ventral tegmental area, ventral pallidum, nucleus of the solitary tract, parabrachial nucleus, and the amygdala.

Beyond the central effects on food intake and appetite, opioids also inhibit peripheral secretion of the main catabolic hormones, insulin (Schleicher, 1989; Garcia-Barrado et al, 2002; Guido et al, 2006) and leptin (Houshyar et al, 2003) and desensitize insulin receptors (Li et al 2003), potentially by reducing the levels of adiponectin (Housova et al, 2005). The latter is an adipocyte-derived hormone (Maeda et al, 1996) possessing insulin receptor sensitizing properties (Berg et al, 2002; Haluzik et al, 2004), and its levels appear to be diminished even in drug-free schizophrenics (Cohn et al, 2006).

Without being bound by any mechanism, we believe opioidergic mechanisms of obesity are pertinent for schizophrenic patients because robust elevations of endogenous opiate concentrations in the cerebral spinal fluid and in plasma (Terenius et al, 1976; Lindstrom et al, 1978, 1986; Rimon et al, 1980; Brambilla et al, 1984; Marchesi et al, 1995) is a relatively consistent clinical finding in this illness. Opiate levels tend to parallel the severity of psychosis (Terenius et al, 1976; Lindstrom et al, 1978; Rimon et al, 1980; Marchesi et al, 1995), suggesting involvement of this neurochemical effect in schizophrenia neuropathology (Volavka et al, 1979; Schmauss and Emrich, 1985; Nemeroff and Bissette, 1988).

One possible involvement is through opiate's interference with the neurotrophines (e.g., BDNF) supporting neuronal survival (Weickert et al, 2003; Angelucci et al, 2005) with consequential damage of mesolimbic dopaminergic neurons (Sklair-Tavron et al, 1996). Furthermore, similarly to methadone-maintained patients (Willenbring et al, 1989; Zador et al, 1996), exaggerated opioidergic activity may enhance hedonic preference for sweet and fatty foods (Doyle et al, 1993; Pecina and Berridge, 1995; Kelley et al, 2002; Will et al, 2003). The consumption of these foods further reduces BDNF efficiency in preventing neuronal death (Molteni et al, 2002) and in regulating reward function (Horger et al, 1999; Kernie et al, 2000; Nakagawa et al, 2003), glucose metabolism (Tonra et al, 1999; Nakagawa et al, 2000; Ono et al, 2000), appetitive behaviors (Eisch et al, 2003; Itoh et al, 2004), and other important homeostatic processes (Xu et al, 2003).

Another manifestation of alterations in endogenous opioids in schizophrenics may relate to pain insensitivity. We believe this and other aberrations in protective mechanisms afforded by the pain system are yet another aspect of excessive/altered endogenous opioid function in schizophrenia (Davis et al, 1979; Evans, 1980; Davis and Buchsbaum, 1981; Fishbain, 1982; Bickerstaff et al, 1988; Rosenthal et al, 1990; Dworkin, 1994; Kudoh et al, 2000; Torrey, 2002; Singh et al, 2006; Haslam, 1798, 1809 cited in Torrey, 2002; Kraepelin, 1919 cited in Hooley and Delgado, 2001; Bleuler, 1924 cited in Hooley and Delgado, 2001; Davis, 1983; and Wiegant et al, 1992). This view is supported clinically by reversal of pain insensitivity by opioid antagonism (Davis et al, 1979) and by molecular abnormalities in specific opioid genes, for example, prodynorphin (Ventriglia et al, 2002) or proenkephalin (Mikesell et al, 1996) in schizophrenic patients. Importantly, pain problems in schizophrenics are apparent in the context of real-life situations, for example, tissue damage following surgical treatment (Kudoh et al, 2000; Murthy et al, 2004), and their consequences range from finger burns caused by cigarette smoking (Jenkins et al, 1996) to such grave medical outcomes as silent myocardial infarction (Marchand, 1955) or delays in management of abdominal emergencies (Katz et al, 1990; Bickerstaff et al, 1988) that could be followed by perforated bowel (Rosenthal et al, 1990) and ruptured appendix (Geschwind, 1977).

Among the complex mix of SGAs' pharmacological properties, these compounds may be associated with enhancements in the opioidergic activity, which could further deteriorate the pre-existing metabolic, hedonic, sensory alterations in patients with schizophrenia and be involved in insulin resistance (newcomer et al, 2002; Henderson et al, 2005a, 2006) and adiponectin (Richards et al, 2006) decrements associated with these drugs. Several lines of clinical and preclinical evidence support our view. These include clinical presentation of olanzapine overdose, which is similar to opioid intoxication (O'Malley et al, 1999; Kochhar et al, 2002; Palenzona et al, 2004; Theisen et al, 2005) and analgesic/antinociceptive properties of olanzapine observed in both human (Kiser et al, 2001; Silberstein et al, 2002; Khojainova et al, 2002; Gorski and Willis, 2003; Fishbain et al, 2004) and rodent (Schreiber et al, 1999; Weizman et al, 2003) models and partially ascribed to the opioid mechanisms (Schreiber et al, 1999; Weizman et al, 2003).

Treatment of Psychiatric Disorders

The methods of the invention may be employed for any psychiatric disorder in which SGAs are employed as a treatment or in which opioidergic function results in detrimental sequelae. Examples of psychiatric disorders treated with SGAs include schizophrenia, autism, psychosis, schizoaffective disorder, mood disorders (e.g., bipolar disorder), anxiety disorders (e.g. post-traumatic stress, obsessive-compulsive), dementia, sleep disorders, eating disorders, drug/alcohol abuse and dependence, impulse control disorders, personality disorders (e.g., borderline and antisocial), and, for the purposes of this invention, neuropathic pain.

In general, the subject being treated with the SGA will be under the continuing care of a physician. In certain embodiments, the subject will not be suffering from comorbid substance abuse, dependence, or withdrawal, such as alcohol, opioid, or cocaine abuse, dependence, or withdrawal. Certain of these disorders, e.g., schizophrenia, are associated with sequelae, whether or not treated with an SGA. Such sequelae include sequelae of weight gain, including obesity, metabolic syndrome, insulin resistance, abdominal adiposity, impaired, glucose tolerance, dyslipidaemia, hypercholesterolemia, diabetes, and hypertension, and also pain insensitivity. In certain embodiments, treatment will be limited to subjects having a body mass index (BMI) greater than or equal to 30 kg/m$^2$ or a BMI greater than or equal to 27 kg/m$^2$ plus one symptom of the Metabolic Syndrome, e.g., fasting blood sugar>125, hypertension, or dyslipidemia. Treatment may also be limited to subjects whose weight gain is attributable to SGA administration, determined for example by past psychiatric and medical records of pretreatment body weight.

Efficacy of treatment may be assessed by reduction in weight or BMI, subjective pain ratings, waist, waist/hip ratio, fasting blood glucose, LDL cholesterol, HDL cholesterol, triglycerides, fat body mass, insulin, leptin, and/or food intake. Weight may be measured using a digital electronic scale and height with a Harpenden stadiometer, calibrated on a weekly basis. Circumferences may be measured at the narrowest waist, umbilicus waist, iliac waist, and broadest hip (buttocks). Waist-hip ratio may be calculated as iliac waist measure relative to the widest hip circumference. Body composition (lean and fat body mass) may be determined by bioelectric impedance analysis (RJL Systems, Clinton Township, Mich.). A 4-day food assessment may be collected from each subject and analyzed using an extensive nutrient data base (Schakel et al, 1988; Henderson et al, 2005a). Methods for determining pain sensitivity are described herein.

Second Generation Antipsychotic Agents

SGAs are employed to treat a variety of disorders, as described, herein. Exemplary SGAs include sulpiride, amisulpride, clozapine, olanzapine, aripirazole, ziprasidone, quetiapine, risperidone, remoxipride, zotepine, sertindole, and iloperidone. Use of SGAs may, however, result in, exacerbate, or not address detrimental sequelae, such as sequelae of weight gain and pain insensitivity, in a psychiatric disorder. These sequelae may in turn result in patients stopping therapy or developing additional health problems, potentially more serious than those being treated by the SGA.

Opioid Receptor Antagonists

Opioid antagonism enhances sensitivity of opioid receptors (Zukin et al, 1982; Lesscher et al, 2003) and diminishes tolerance and physical dependence on opioids (Powell et al, 2002). In rodent studies, opioid antagonists block hedonic responses to sweet foods and sugar-induced analgesia (Blass et al, 1987; Blass and Fitzgerald, 1988) without affecting total energy intake (Berridge, 1996; Rodefer et al, 1999). Moreover, all but one human study (Hetherington et al, 1991) employing opioid receptor antagonists, including naloxone (Thompson et al, 1982; Trenchard and Silverstone, 1983; Cohen et al, 1985; Drewnowski et al, 1992; MacIntosh et al, 2001), naltrexone (Fantino et al, 1986; Jonas and Gold, 1986; Melchior et al, 1989; Bertino et al, 1991; Chatoor et al, 1994; Yeomans and Gray, 1996, 1997), and nalmefene (Yeomans et al, 1990; Yeomans and Wright, 1991), found significant decreases in caloric intake (Yeomans and Gray, 2002). In clinical populations, opioid antagonism successfully curbed excessive food intake in bulimic patients (Jonas and Gold, 1986; Chatoor et al, 1994; Marrazzi et al, 1995a, 1995b) as well as opioid (Shufman et al, 1994) and alcohol (O'Mara and Wesley, 1994) abuse. Above and beyond their dietary effects, opioid antagonists may also contribute to weight reduction by reasons of diminished hyperinsulinemia and improved insulin sensitivity (Cucinelli et al, 2002; Fruzzetti et al, 2002).

Any opioid receptor antagonist may be employed in the methods and compositions of the invention. Exemplary opioid receptor antagonists include diprenorphine, naloxone, naltrexone, β-chlornaltrexamine (β-CNA), WIN44,441-3 (Faden, et al. Neurology 35:1311-1315, 1985.), nalmefene, alvimopan (ADL 8-2698), and methylnatrexone. In addition, an opioid receptor antagonist may be predominately active as a $\mu$, $\delta$, or $\kappa$ opioid receptor antagonist, although such agents may also be active at other receptors as well. Naltrexone is a well tolerated opioid antagonist lacking any abuse potential, which is active on $\mu$- and $\kappa$-opioid receptors, and to some extent at $\delta$-opioid receptors. $\mu$-opioid receptor specific antagonists include cyprodime, naloxonazine, naloxazone, β-funaltrexamine (β-FNA), and CTOP (Pelton, et al. J. Med. Chem. 29: 2370-2375, 1986). $\kappa$-opioid receptor antagonists include naltrindole, ICI174,864 (Evans, et al. The opioid peptides. In: Pasternak G W, ed. *The opiate receptors*. Clifton, N.J.: Humana Press, 1988:23-74), 7-benzylidenenaltrexone (BNTX), and naltriben (NTB). $\kappa$-opioid receptor antagonists include nor-binaltorphimine (norBNI), 5'-guanidinonaltrindole (GNTI), (−)-(1R,5R,9R)-5,9-diethyl-2-(3-furylmethyl)-2-hydroxy-6,7-benzomorphan (MR 2266) (Merz, et al. Advances in biochemical psychopharmacology, Vol 8:91-107), and a triethylenedioxy derivative of naltrexamine (TENA) (Portoghese et al. Life Sciences 36:801-5). In addition, partial agonists/antagonists may also be employed. Exemplary partial agonists include butorphanol, dezocine, nalbulphine, nalorphine, pentazocine, and buprenorphine.

Pain Insensitivity

Pleasurable effects of palatable food are conveyed to the frontotemporal cortical structures through $\mu$-opioid neurotransmission within the scattered network of subcortical and brainstem nuclei. Thus, patients with enhanced opioidergic drive (reflected as diminished activation in reward and sensory regions) tend to consume more unhealthy palatable nutrition resulting in greater body weight gain. Hence, at baseline in subjects with schizophrenia, subjective pain ratings in response to noxious thermal stimulus will be negatively correlated with the weight and the body mass index. Thus, a normally painful stimulus will be sensed as less painful in schizophrenics vs. healthy controls. We believe probing reward function will be predictive of therapeutic efficacy of the methods described herein.

The experience of pain is thought to be related to the underlying status of the brain reward system (Le Magnen et al, 1980; Gear et al, 1999; Koyama et al, 2001). Evidence linking reward with pain arises from neuroimaging data, in which a shared neuroanatomic substrate was demonstrated for reward and pain by observing that both putative reward circuits and classic pain circuitry were activated when healthy controls were exposed to noxious thermal stimuli (Becerra et al, 2001). In schizophrenia, however, we believe that noxious afferents are not exerting the effects on reward circuitry that are observed in healthy people, which could be yet another aspect of excessive/altered endogenous opioid function (Davis et al, 1979; Davis and Buchsbaum, 1981; Davis, 1983; Wiegant et al, 1992).

Without being bound by any mechanism, we believe that a mesolimbic hyperdopaminergic state associated with schizophrenia may render motivational/incentive reward system insensitive to low salience/palatability food. This, together with poor cognitive control from hypofunctional prefrontal cortex and enhanced hedonic impact of food, owing to exaggerated opioidergic drive (clinically manifested as pain insensitivity), may underlie unhealthy eating habits in patients with schizophrenia. Furthermore, treatment with SGAs purportedly improves dopamine-mediated reward aspects, but at the cost of increased appetite and worsened or at least not improved opiodergic capacity, which can further deteriorate metabolic problems.

Further evidence suggests a link between homeostatic and reward functions. Twelve cocaine-dependent individuals received an intravenous bolus of a pharmacological reward, cocaine, and cortisol in a double-blind randomized placebo-controlled and counterbalanced fashion. Their plasma was assayed over the next 120 minutes for the levels of two catabolic hormones, namely insulin and leptin. Cocaine (but not cortisol) injection produced significant decreases in insulin, but not in leptin. Notably, when baseline insulin and leptin levels along with BMIs were considered, they predicted baseline, withdrawal-related cocaine craving, accounting for approximately 76% of the variance, while BMIs predicted cocaine-primed craving and euphoria i.e., high.

It has also been observed that noxious thermal stimuli (46° C.) produced significant signal change in the reward regions as well as in classic pain circuitry in healthy subjects (Becerra et al, 2001). Increases in signal were observed in the extended amygdala and the VTA/periaqueductal gray (PAG), while foci of increased-and decreased signal were observed in the NAc. Early and late phases were observed for signals in most brain regions, with early activation in reward related regions such as the extended amygdala, VTA/PAG and NAc. In contrast, structures associated with somatosensory perception, including somatosensory cortex, thalamus, and insula, showed delayed activation. These data support our view that noxious thermal stimuli may be used as a probe for functional integrity of reward circuitry.

The use of the thermal pain probe as a proxy to measure opioidergic status has ecological validity given that patients with excessive opioidergic drive like those treated with methadone consistently display enhanced hedonic preference for sweet and fatty foods (Willenbring et al, 1989; Zador et al, 1996).

Accordingly, the invention also features methods for determining the therapeutic efficacy of treatment with an opioid antagonist. For example, weight loss will be correlated with subjective pain ratings. In addition, we believe that normalization of the pain ratings after initiation of treatment, e.g., after 1, 2, 3, 4, 5, or 6 weeks, will be predictive for weights and BMIs later in treatment, e.g., at 12 weeks. Thus, patients who ultimately respond to naltrexone augmentation (e.g., as determined at 12 weeks) will show significant, partial normalization in responses to the sensory stimulus earlier in treatment, e.g., at 6 weeks. These effects may also be used to screen persons at risk for the development of obesity, and those found to possess high vulnerability for excessive body weight gain (i.e., increased opioidergic drive) may be counseled to avoid palatable food exposure (primary prevention), or targeted for early intervention with opioid antagonists even in the presence of mild weight problems (secondary prevention). Levels of pain sensitivity may be measured relative to a healthy control value, a typical diseased value, or to an individual's level measured previously, e.g., before onset of therapeutic treatment.

Quantitive Sensory Testing (QST) may be performed to determine the temperatures of subjects' heat pain thresholds. A standard clinical evaluation program may be used to determine pain thresholds. This program includes a series of hot stimuli that are delivered from a baseline temperature of 32°C. The subjects control the heating unit with a computer mouse and tap the mouse button at the first perception of pain. Each stimulus is typically delivered 3-5 times. Thermal stimuli may be delivered to a 3 cm×3 cm surface on the dorsum of the left hand, using a commercially available Peltier thermode with a thermoconducting surface (MEDOC TSA 2001, Haifa, Israel). This device delivers precise temperatures to the skin via a thermal probe called a thermode. In one protocol, three temperatures will be used: 1) 35° C., which is the baseline temperature; 2) 41° C., which produces a "warm" stimulus; and 3) 46° C., which produces a "noxious" heat stimulus. Stimuli may be delivered in the following order: first, subjects receive a series of four alternating stimuli of the baseline 35° C. temperature for 36 seconds and the 41° C. temperature for 29 seconds. After five minutes, this paradigm may be repeated with four sets of the baseline 35° C. temperature and the higher 46° C. temperature. A ramp and hold method, with a rate of temperature rise of 4° C./sec may be used. The alternating series with 410° C. typically precedes the series with 46° C., as the higher temperature may produce hyperalgesia whereas 41° C. does not affect attenuation from application of a 46° C. stimulus. After each stimulus is delivered, subjects rate with a four-button button-press their subjective experience of pain intensity. Ratings range from 0=no pain to 4=unbearable pain. Prior to beginning the thermal experimental paradigm, subjects may be connected to an ECG, pupilometer and galvanic skin response apparatus. These three devices may be used to monitor physiological parameters, and to correlate these parameters with thermal stimulation and pain intensity ratings. Change scores may be computed for pre-to post-"noxious" stimulus and pre-to post-"warm" stimulus. Other methods for determining pain insensitivity are known in the art.

Administration

Conventional pharmaceutical practice is employed to provide suitable formulations or compositions for administration to patients. Oral administration is preferred, but any other appropriate route of administration may be employed, for example, transdermal (e.g., via a patch), parenteral, intravenous, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of liquids, tablets, or capsules; and for intranasal formulations, in the form of powders, nasal drops, or aerosols. In addition, compounds useful in the methods described herein also include encapsulated compounds, e.g., liposome- or polymer-encapsulated compounds. Useful compounds further include those linked (e.g., covalently or non-covalently) to various antibodies, ligands, or other targeting and enveloping or shielding agents (e.g., albumin or dextrose), to allow the compound to reach the target site (e.g., the central nervous system) prior to being removed from the blood stream, e.g., by the kidneys and liver, and prior to being degraded.

Methods well known in the art for making formulations are described, for example, in *Remington: The Science and Practice of Pharmacy* (20th ed.) ed. A. R. Gennaro, Lippincott: Philadelphia 2003. Formulations for parenteral administration may, for example, contain excipients, sterile water, saline, polyalkylene glycols such as polyethylene glycol, oils of vegetable origin, or hydrogenated naphthalenes.

Slow release or extended release delivery systems may be utilized, e.g., to provide a substantially constant release of drug over a period of time. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In general, the compounds of the invention are administered at a dosage appropriate to achieve the desired effect and are typically administered in unit dosage form. For SGAs, the dosage preferably ranges from 1 mg per day to 3000 mg per day, e.g., at most 2000 mg, 1000 mg, 600 mg, 500 mg, 100 mg, 50 mg, 10 mg, or 5 mg. For example, olanzapine may be administered at 2-50 mg/day, e.g., 5-15 mg/day or 10-20 mg/day; sulpiride may be administered at 10-3000 mg/day, e.g., 100-2400 mg/day, amisulpride may be administered at 5-1000 mg/day, e.g., 50-300 mg/day, clozapine may be administered at 5-2000 mg/day, e.g., 12.5-900 mg/day, aripirazole may be administered at 2-100 mg/day, e.g., 10-30 mg/day, ziprasidone may be administered at 2-1000 mg/day, e.g., 20-200 mg/day, quetiapine may be administered at 15-2000 mg/day, e.g., 150-700 mg/day, risperidone may be administered at 1-16, e.g., 4-6 mg/day, remoxipride may be administered at 5-2000 mg/day, e.g., 75-600 mg/day, zotepine may be administered at 15-1000 mg/day, e.g., 150-300 mg/day, sertindole may be administered at 1-200 mg/day, e.g., 4-20 mg/day, and iloperidone may be administered at 1-100 mg/day, e.g., 2-32 mg/day. For opioid receptor antagonists, the dosage preferably ranges from 0.0001 to 1000 mg per day, e.g., at most 100 mg, 10 mg, 1 mg, 0.1 mg, 0.01 mg, or 0.001 mg. For example, naltrexone may be administered at 0.0001-500 mg/day, e.g., 25-50 mg/day, naloxone may be administered at 0.001-100 mg/day, e.g., 0.1 to 10 mg/day, nalmefene may be administered at 0.0001-10 mg/day, e.g., 0.001-1 mg/day, butorphanol may be administered at 0.1-100 mg/day, e.g., 1-32 mg/day, dezocine may be administered at 0.1-1000 mg/day, e.g., 5-120 mg/day, nalbulphine may be administered at 1-1000 mg/day, e.g., 10-160 mg/day, and buprenorphine maybe administered at 0.01-10 mg/day, e.g., 0.3 to 1.2 mg/day. In one embodiment, 50 mg of naltrexone is administered in conjunction with 10-20 mg of olanzapine. Naltrexone may also be administered as an extended release injectable form, e.g., Vivitrol® (380 mg gluteal IM injection), or as a subcutaneous implant, e.g., VP004 (Valera). Other opioid receptor antagonists may be administered in similar fashion. Furthermore, the ratio of amount of opioid receptor antagonist to SGA may be at most 1:1, 1:10, 1:100, 1:1,000, 1:10,000, 1:100,000, 1:1,000,000, 1:10,000,000, 1:100,000,000, or 1:1,000,000,000. The two compounds may be administered concomitantly, either in the same or different formulations, or at different times.

The exact dosage of the compound may be dependent, for example, upon the age and weight of the recipient, the route of administration, and the severity and nature of the symptoms to be treated. Other factors that may affect the dosing include age of illness' onset; duration of illness, diagnostic subtype, severity of symptoms, dose and plasma levels of SGA, past/current substance use and smoking habits; current use of other medications; pain threshold; affective symptom severity; dietary habits, socioeconomic status; and physical activity and other life style-related factors.

In general, the dosage selected should be sufficient to prevent, ameliorate, or treat a particular indication, or one or more symptoms thereof, or effect a particular outcome without producing significant toxic or undesirable side effects. In certain embodiments, the SGA, opioid receptor antagonist, or both may be administered in an individually subtherapeutically effective amount. As noted above, the preferred route of administration for most indications is oral.

In certain embodiments, additional therapeutic compounds may be employed in the methods of the invention, such as zolpidem tartrate, e.g., up to a maximum dose of 10 mg/day, or zaleplon, e.g., up to a maximum dose of 20 mg/day for insomnia as clinically indicated. Other examples include lorazepam for agitation at the discretion of the treating clinician. Administration of lorazepam within six hours of the administration of rating scales is desirably avoided. In other embodiments, concomitant administration of other therapeutic compounds is not employed. For example, medications or drugs with prominent orexigenic/anorexigenic effects, e.g., anticholinergics, insulin, oral hypoglycemics, amphetamines, mood stabilizers, opioid analgesics, anti-depressants including tricyclics, SSRIs, MAO inhibitors, bupropion, and mirtazepine, may be excluded from the methods described herein.

References

Angelucci, F., Brene, S., and Mathe, A. A. (2005). BDNF in schizophrenia, depression and corresponding animal models. Mol Psychiatry, 10(4):345-352.

Becerra, L., Breiter, H. C., Wise, R., Gonzalez, R. G., and Borsook, D. (2001). Reward circuitry activation by noxious thermal stimuli. Neuron, 32(5):927-946.

Berg, A. H., Combs, T. P., and Scherer, P. E. (2002). ACRP30/adiponectin: an adipokine regulating glucose and lipid metabolism. Trends Endocrinol Metab, 13(2):84-89.

Berridge, K. C. (1996). Food reward: brain substrates of wanting and liking. Neurosci Biobehav Rev, 20(1):1-25.

Berridge, K. C. (2003). Pleasures of the brain. Brain Cogn, 52(1):106-128.

Berridge, K. C., and Robinson, T. E. (2003). Parsing reward. Trends Neurosci, 26(9):507-513

Bertino, M., Beauchamp, G. K., and Engelman, K. (1991). Naltrexone, an opioid blocker, alters taste perception and nutrient intake in humans. Am J Physiol, 261 (1 Pt 2):R59-R63.

Bickerstaff, L. K., Harris, S.C., Leggett, R. S., and Cheah, K. C. (1988). Pain insensitivity in schizophrenic patients. A surgical dilemma. Arch Surg, 123(1):49-51.

Blass, E., Fitzgerald, E., and Kehoe, P. (1987). Interactions between sucrose, pain and isolation distress. Pharmacol Biochem Behav, 26(3):483-489.

Blass, E. M., and Fitzgerald, E. (1988). Milk-induced analgesia and comforting in 10-day-old rats: opioid mediation. Pharmacol Biochem Behav, 29(1):9-13.

Bleuler, E. (1924). Textbook of Psychiatry (A. A. Brill, Trans). New York: The Macmillan Company. (Reprinted 1988 by the Classics of Psychiatry and Behavioral Sciences Library, New York).

Brambilla, F., Facchinetti, F., Petraglia, F., Vanzulli, L., Genazzani, A. R. (1984). Secretion pattern of endogenous opioids in chronic schizophrenia. Am J Psychiatry, 141(10): 1183-1189.

Chatoor, I., Herman, B. H., and Hartzler, J. (1994). Effects of the opiate antagonist, naltrexone, on binging antecedents and plasma beta-endorphin concentrations. J Am Acad Child Adolesc Psychiatry, 33(5):748-752.

Cohen, M. R., Cohen, R. M., Pickar, D., and Murphy, D. L. (1985). Naloxone reduces food intake in humans. Psychosom Med, 47(2):132-138.

Cohn, T. A., Remington, G., Zipursky, R. B., Azad, A., Connolly, P., and Wolever, T. M. (2006). Insulin resistance and adiponectin levels in drug-free patients with schizophrenia: A preliminary report. Can J Psychiatry, 51(6):382-386.

Cucinelli, F., Soranna, L., Perri, C., Romualdi, D., Barini, A., Mancuso, S., and Lanzone, A. (2002). Naloxone decreases insulin secretion in hyperinsulinemic postmenopausal women and may positively affect hormone replacement therapy. Fertil Steril, 78(5):1017-1024.

Davis, G. C. (1983). Endorphins and pain. Psychiatr Clin North Am, 6(3):473-487.

Davis, G. C., and Buchsbaum, M. S. (1981). Pain sensitivity and endorphins in functional psychoses. Mod Probl Pharmacopsychiatry, 17:97-108.

Davis, G. C., Buchsbaum, M. S., van Kammen, D. P., and Bunney Jr, W. E. (1979). Analgesia to pain stimuli in schizophrenics and its reversal by naltrexone. Psychiatry Res, 1(1): 61-69.

Doyle, T. G., Berridge, K.C., and Gosnell, B. A. (1993). Morphine enhances hedonic taste palatability in rats. Pharmacol Biochem Behav, 46(3):745-749.

Drewnowski, A., Krahn, D. D., Demitrack, M. A., Nairn, K., and Gosnell, B. A. (1992). Taste responses and preferences for sweet high-fat foods: evidence for opioid involvement. Physiol Behav, 51(2):371-379.

Dworkin, R. H. (1994). Pain insensitivity in schizophrenia: a neglected phenomenon and some implications. Schizophr Bull, 20(2):235-248.

Eisch, A. J., Bolanos, C. A., de Wit, J., Simonak, R. D., Pudiak, C. M., Barrot, M., Verhaagen, J., and Nestler, E. J. (2003). Brain-derived neurotrophic factor in the ventral midbrain-nucleus accumbens pathway: a role in depression. Biol Psychiatry, 54(10):994-1005.

Elman, I., Borsook, D., and Lukas, S. E. (2006). Food Intake and Reward Mechanisms in Patients with Schizophrenia: Implications for Metabolic Disturbances and Treatment with Second-Generation Antipsychotic Agents. Neuropsychopharmacology. [Epub 2006 Mar. 15].

Evans, D. L. (1980). Pain insensitivity in psychotic patients. Am J Psychiatry, 137(4):507-508.

Fantino, M., Hosotte, J., and Apfelbaum, M. (1986). An opioid antagonist, naltrexone, reduces preference for sucrose in humans. Am J Physiol, 251(1 Pt 2):R91-R96.

Fishbain, D. A. (1982). Pain insensitivity in psychosis. Ann Emerg Med, 11(11):630-632.

Fishbain, D. A., Cutler, R. B., Lewis, J., Cole, B., Rosomoff, R. S., and Rosomoff, H. L. (2004). Do the second-generation "atypical neuroleptics" have analgesic properties? A structured evidence-based review. Pain Med, 5(4):359-365.

Fruzzetti, F., Bersi, C., Parrini, D., Ricci, C., and Genazzani, A. R. (2002). Effect of long-term naltrexone treatment on endocrine profile, clinical features, and insulin sensitivity in obese women with polycystic ovary syndrome. Fertil Steril, 77(5):936-944.

Garcia-Barrado, M. J., Iglesias-Osma, M. C., Rodriguez, R., Martin, M., and Moratinos, J. (2002). Role of mu-opioid receptors in insulin release in the presence of inhibitory and excitatory secretagogues. Eur J Pharmacol, 448(1):95-104.

Gear, R. W., Aley, K. O., and Levine, J. D. (1999). Pain-induced analgesia mediated by mesolimbic reward circuits. J Neurosci, 19(16):7175-7181.

Geschwind, N. (1977). Insensitivity to pain in psychotic patients. N Engl J Med, 296(25):1480.

Gorski, E. D., and Willis, K. C. (2003). Report of three case studies with olanzapine for chronic pain. J Pain, 4(3):166-168.

Guido, M., Romualdi, D., and Lanzone, A. (2006). Role of opioid antagonists in the treatment of women with glucoregulation abnormalities. Curr Pharm Des, 12(8):1001-1012.

Haluzik, M., Parizkova, J., and Haluzik, M. M. (2004). Adiponectin and its role in the obesity-induced insulin resistance and related complications. Physiol Res, 53(2):123-129.

Haslam, J. (1798). Observations on insanity: With practical remarks on the disease, and an account of the morbid appearances on dissection. London, England: F. and C. Rivington.

Haslam, J. (1809). Observations on Madness and Melancholy (pp. 49, 140). London, England: J Callow. (Reprinted 1976 by the Classics of Psychiatry and Behavioral Science Library, New York).

Henderson, D. C., Cagliero, E., Copeland, P. M., Borba, C. P., Evins, E., Hayden, D., Weber, M. T., Anderson, E. J., Allison, D. B., Daley, T. B., Schoenfeld, D., and Goff, D. C. (2005a). Glucose metabolism in patients with schizophrenia treated with atypical antipsychotic agents: a frequently sampled intravenous glucose tolerance test and minimal model analysis. Arch Gen Psychiatry, 62(1):19-28.

Henderson, D. C., Copeland, P. M., Borba, C. P., Daley, T. B., Nguyen, D. D., Cagliero, E., Evins, A. E., Zhang, H., Hayden, D. L., Freudenreich, O., Cather, C., Schoenfeld, D. A., and Goff, D. C (2006). Glucose metabolism in patients with schizophrenia treated with olanzapine or quetiapine: a frequently sampled intravenous glucose tolerance test and minimal model analysis. J Clin Psychiatry, 67(5):789-797.

Hetherington, M. M., Vervaet, N., Blass, E., and Rolls, B. J. (1991). Failure of naltrexone to affect the pleasantness or intake of food. Pharmacol Biochem Behav, 40(1):185-190.

Hooley, J. M., and Delgado, M. L. (2001). Pain insensitivity in the relatives of schizophrenia patients. Schizophr Res, 47(2-3):265-273.

Horger, B. A., Iyasere, C. A., Berhow, M. T., Messer, C. J., Nestler, E. J., and Taylor, J. R. (1999). Enhancement of locomotor activity and conditioned reward to cocaine by brain-derived neurotrophic factor. J Neurosci, 19(10):41 10-4122.

Houshyar, H., Gomez, F., Manalo, S., Bhargava, A., and Dallman, M. F. (2003). Intermittent morphine administration induces dependence and is a chronic stressor in rats. Neuropsychopharmacology, 28(11):1960-1972.

Housova, J., Wilczek, H., Haluzik, M. M., Kremen, J., Krizova, J., and Haluzik, M. (2005). Adipocyte-derived hormones in heroin addicts: the influence of methadone maintenance treatment. Physiol Res, 54(1):73-78.

Itoh, K., Hashimoto, K., Kumakiri, C., Shimizu, E., and Iyo, M. (2004). Association between brain-derived neurotrophic factor 196 G/A polymorphism and personality traits in healthy subjects. Am J Med Genet B Neuropsychiatr Genet, 124(1):61-63.

Jenkins, L., Malik, M. A., Lik, M., and Vaczi, P. (1996). Multiple cigarette burn wounds in a chronic paranoid schizophrenic. S Afr Med J, 86(5):572.

Jonas, J. M., and Gold, M. S. (1986). Naltrexone reverses bulimic symptoms. Lancet, 1(8484):807.

Kampov-Polevoy A B, Tsoi M V, Zvartau E E, Neznanov N G, Khalitov E. Sweet liking and family history of alcoholism in hospitalized alcoholic and non-alcoholic patients. Alcohol Alcohol. 2001;36(2):165-70.

Katz, E., Kluger, Y., Rabinovici, R., Stein, D., and Gimmon, Z. (1990).
Acute surgical abdominal disease in chronic schizophrenic patients: a unique clinical problem. Isr J Med Sci, 26(5):275-277.

Kelley, A. E., Bakshi, V. P., Haber, S. N., Steininger, T. L., Will, M. J., and Zhang, M. (2002). Opioid modulation of taste hedonics within the ventral striatum. Physiol Behav, 76(3): 365-377.

Kernie, S. G., Liebl, D. J., and Parada, L. F. (2000). BDNF regulates eating behavior and locomotor activity in mice. EMBO J, 19(6): 1290-1300.

Khojainova, N., Santiago-Palma, J., Kornick, C., Breitbart, W., and Gonzales, G. R. (2002). Olanzapine in the management of cancer pain. J Pain Symptom Manage, 23(4):346-350.

Kiser, R. S., Cohen, H. M., Freedenfeld, R. N., Jewell, C., and Fuchs, P. N. (2001). Olanzapine for the treatment of fibromyalgia symptoms. J Pain Symptom Manage, 22(2): 704-708.

Kochhar, S., Nwokike, J. N., Jankowitz, B., Sholevar, E. H., Abed, T., and Baron, D. A. (2002). Olanzapine overdose: a pediatric case report. J Child Adolesc Psychopharmacol, 12(4):351-353.

Koyama, T., Kato, K., Tanaka, Y. Z., and Mikami, A. (2001). Anterior cingulate activity during pain-avoidance and reward tasks in monkeys. Neurosci Res, 39(4):421-430.

Kraepelin, E., (1919). Dementia Praecox and Paraphrenia. Edinburgh, Scotland: A. S. Livingstone. (Reprinted 1989 by the Classics of Psychiatry and Behavioral Sciences Library, New York).

Kudoh, A., Ishihara, H., and Matsuki, A. (2000). Current perception thresholds and postoperative pain in schizophrenic patients. Reg Anesth Pain Med, 25(5):475-479.

Le Magnen, J., Marfaing-Jallat, P., Miceli, D., and Devos, M. (1980). Pain modulating and reward systems: a single brain mechanism? Pharmacol Biochem Behav, 12(5):729-733.

Lesscher, H. M., Bailey, A., Burbach, J. P., Van Ree, J. M., Kitchen, I., Gerrits, M. A. (2003). Receptor-selective changes in mu-, delta-and kappa-opioid receptors after chronic naltrexone treatment in mice. Eur J Neurosci, 17(5):1006-1012.

Li, Y., Eitan, S., Wu, J., Evans, C. J., Kieffer, B., Sun, X., and Polakiewicz, R. D. (2003). Morphine induces desensitization of insulin receptor signaling. Mol Cell Biol, 23(17): 6255-6266.

Lindstrom, L. H., Besev, G., Gunne, L. M., and Terenius, L. (1986). CSF levels of receptor-active endorphins in schizophrenic patients: correlations with symptomatology and monoamine metabolites. Psychiatry Res, 19(2):93-100.

Lindstrom, L. H., Widerlov, E., Gunne, L. M., Wahlstrom, A., and Terenius, L. (1978). Endorphins in human cerebrospinal fluid: clinical correlations to some psychotic states. Acta Psychiatr Scand, 57(2):153-164.

MacIntosh, C. G., Sheehan, J., Davani, N., Morley, J. E., Horowitz, M., and Chapman, I. M. (2001). Effects of aging on the opioid modulation of feeding in humans. J Am Geriatr Soc, 49(11):1518-1524.

Maeda, K., Okubo, K., Shimomura, I., Funahashi, T., Matsuzawa, Y., and Matsubara, K. (1996). cDNA cloning and expression of a novel adipose specific collagen-like factor, apM1 (AdiPose Most abundant Gene transcript 1). Biochem Biophys Res Commun, 221(2):286-289.

Marchand, W. E. (1955). Occurrence-of painless myocardial infarction in psychotic patients. N Engl J Med, 253(2): 51-55.

Marchesi, G. F., Santone, G., Cotani, P., Giordano, A., and Chelli, F. (1995). The therapeutic role of naltrexone in negative symptom schizophrenia. Prog Neuropsychopharmacol Biol Psychiatry, 19(8):1239-1249.

Marrazzi, M. A., Bacon, J. P., Kinzie, J., and Luby, E. D. (1995a). Naltrexone use in the treatment of anorexia nervosa and bulimia nervosa. Int Clin Psychopharmacol, 10(3):163-172.

Marrazzi, M. A., Kinzie, J., and Luby, E. D. (1995b). A detailed longitudinal analysis on the use of naltrexone in the treatment of bulimia. Int Clin Psychopharmacol, 10(3):173-176.

Masand PS, Culpepper L, Henderson, Lee S, Littrell K, Newcomer J W, Rasgon N. (2005). Metabolic and endocrine disturbances in psychiatric disorders: a multidisciplinary approach to appropriate atypical antipsychotic utilization. CNS Spectr, 10(10):suppl141-15.

Melchior, J. C., Fantino, M., Rozen, R., Igoin, L., Rigaud, D., and Apfelbaum, M. (1989). Effects of a low dose of naltrexone on glucose-induced anesthesia and hunger in humans. Pharmacol Biochem Behav, 32(1):117-121.

Mikesell, M. J., Sobell, J. L., Sommer, S. S., and McMurray, C. T. (1996). Identification of a missense mutation and several polymorphisms in the proenkephalin A gene of schizophrenic patients. Am J Med Genet, 67(5):459-467.

Molteni, R., Barnard, R. J., Ying, Z., Roberts, C. K., and Gomez-Pinilla, F. (2002). A high-fat, refined sugar diet reduces hippocampal brain-derived neurotrophic factor, neuronal plasticity, and learning. Neuroscience, 112(4):803-814.

Murthy, B. V., Narayan, B., and Nayagam, S. (2004). Reduced perception of pain in schizophrenia: its relevance to the clinical diagnosis of compartment syndrome. Injury, 35(11): 1192-1193.

Nakagawa, T., Ogawa, Y., Ebihara, K., Yamanaka, M., Tsuchida, A., Taiji, M., Noguchi, H., and Nakao, K. (2003). Anti-obesity and anti-diabetic effects of brain-derived neurotrophic factor in rodent models of leptin resistance. Int J Obes Relat Metab Disord, 27(5):557-565.

Nakagawa, T., Tsuchida, A., Itakura, Y., Nonomura, T., Ono, M., Hirota, F., Inoue, T., Nakayama, C., Taiji, M., and Noguchi, H. (2000). Brain-derived neurotrophic factor regulates glucose metabolism by modulating energy balance in diabetic mice. Diabetes, 49(3):436-444.

Nemeroff, C. B., and Bissette, G. (1988). Neuropeptides, dopamine, and schizophrenia. Ann NY Acad Sci, 537:273-291.

Newcomer, J. W., Haupt, D. W., Fucetola, R., Melson, A. K., Schweiger, J. A., Cooper, B. P., and Selke, G. (2002). Abnormalities in glucose regulation during antipsychotic treatment of schizophrenia. Arch Gen Psychiatry, 59(4):337-345.

O'Malley, G. F., Seifert, S., Heard, K., Daly, F., and Dart, R. C. (1999). Olanzapine overdose mimicking opioid intoxication. Ann Emerg Med, 34(2):279-281.

O'Mara, N. B., and Wesley, L. C. (1994). Naltrexone in the treatment of alcohol dependence. Ann Pharmacother, 28(2): 210-211.

Ono, M., Itakura, Y., Nonomura, T., Nakagawa, T., Nakayama, C., Taiji, M., and Noguchi, H. (2000). Intermittent administration of brain-derived neurotrophic factor ameliorates glucose metabolism in obese diabetic mice. Metabolism, 49(1):129-133.

Palenzona, S., Meier, P. J., Kupferschmidt, H., and Rauber-Luethy, C. (2004). The clinical picture of olanzapine poisoning with special reference to fluctuating mental status. J Toxicol Clin Toxicol, 42(1):27-32.

Pecina, S., and Berridge, K. C. (1995). Central enhancement of taste pleasure by intraventricular morphine. Neurobiology (Bp), 3(3-4):269-280.

Powell, K. J., Abul-Husn, N. S., Jhamandas, A., Olmstead, M. C., Beninger, R. J., and Jhamandas, K. (2002). Paradoxical effects of the opioid antagonist naltrexone on morphine analgesia, tolerance, and reward in rats. J Pharmacol Exp Ther, 300(2):588-596.

Papakostas G I, Petersen T, Iosifescu D V, Bums A M, Nierenberg A A, Alpert J E, Rosenbaum J F, Fava M. Obesity among outpatients with major depressive disorder. Int J Neuropsychopharmacol. 2005;8(1):59-63.

Remington, G. (2006). Schizophrenia, antipsychotics, and the metabolic syndrome: Is there a silver lining? Am J Psychiatry, 163(7):1132-1134.

Richards, A. A., Hickman, I. J., Wang, A. Y., Jones, A. L., Newell, F., Mowry, B. J., Whitehead, J. P., Prins, J. B., and Macdonald, G. A. (2006). Olanzapine treatment is associated with reduced high molecular weight adiponectin in serum: a potential mechanism for olanzapine-induced insulin resistance in patients with schizophrenia. J Clin Psychopharmacol, 26(3):232-237.

Rimon, R., Terenius, L., and Kampman, R. (1980). Cerebrospinal fluid endorphins in schizophrenia. Acta Psychiatr Scand, 61(5):395-403.

Rodefer, J. S., Campbell, U. C., Cosgrove, K. P., and Carroll, M. E. (1999). Naltrexone pretreatment decreases the reinforcing effectiveness of ethanol and saccharin but not PCP or food under concurrent progressive-ratio schedules in rhesus monkeys. Psychopharmacology (Berl), 141(4):436-446.

Rosenthal, S. H., Porter, K. A., and Coffey, B. (1990). Pain insensitivity in schizophrenia. Case report and review of the literature. Gen Hosp Psychiatry, 12(5):319-322.

Singh M K, Giles L L, Nasrallah H A. Pain insensitivity in schizophrenia: trait or state marker? J Psychiatr Pract. 2006; 12(2):90-102.

Saper, C. B., Chou, T. C., and Elmquist, J. K. (2002). The need to feed: homeostatic and hedonic control of eating. Neuron, 36(2):199-211.

Schakel, S. F., Sievert, Y. A., and Buzzard, I. M. (1988). Sources of data for developing and maintaining a nutrient database. J Am Diet Assoc, 88(10):1268-1271.

Schleicher, R. L. (1989). Beta-endorphin inhibits insulin secretion from isolated pancreatic islets. Endocrinology, 124(3):1254-1258.

Schmauss, C., and Emrich, H. M. (1985). Dopamine and the action of opiates: a reevaluation of the dopamine hypothesis of schizophrenia. With special consideration of the role of endogenous opioids in the pathogenesis of schizophrenia. Biol Psychiatry, 20(11):1211-1231.

Schreiber, S., Getslev, V., Backer, M. M., Weizman, R., and Pick, C. G. (1999). The atypical neuroleptics clozapine and olanzapine differ regarding their antinociceptive mechanisms and potency. Pharmacol Biochem Behav, 64(1):75-80.

Schwartz, M. W., and Porte Jr, D. (2005). Diabetes, obesity, and the brain. Science, 307(5708):375-379.

Shufman, E. N., Porat, S., Witztum, E., Gandacu, D., Bar-Hamburger, R., and Ginath, Y. (1994). The efficacy of naltrexone in preventing reabuse of heroin after detoxification. Biol Psychiatry, 35(12):935-945.

Silberstein, S. D., Peres, M. F., Hopkins, M. M., Shechter, A. L., Young, W. B., and Rozen, T. D. (2002). Olanzapine in the treatment of refractory migraine and chronic daily headache. Headache, 42(6):515-518.

Sklair-Tavron, L., Shi, W. X., Lane, S. B., Harris, H. W., Bunney, B. S., and Nestler, E. J. (1996). Chronic morphine induces visible changes in the morphology of mesolimbic dopamine neurons. Proc Natl Acad Sci USA, 93(20):11202-11207.

Sweet, D. C., Levine, A. S., and Kotz, C. M. (2004). Functional opioid pathways are necessary for hypocretin-1 (orexin-A)-induced feeding. Peptides, 25(2):307-314.

Tanda, G., and Di Chiara, G. (1998). A dopamine-mu1 opioid link in the rat ventral tegmentum shared by palatable food (Fonzies) and non-psychostimulant drugs of abuse. Eur J Neurosci, 10(3):1179-1187.

Terenius, L., Wahlstrom, A., Lindstrom, L., and Widerlov, E. (1976). Increased CSF levels of endorphines in chronic psychosis. Neurosci Lett, 3(3):157-162.

Theisen, F. M., Grabarkiewicz, J., Fegbeutel, C., Hubner, A., Mehler-Wex, C., and Remschmidt, H. (2005). Olanzapine overdose in children and adolescents: two case reports and a review of the literature. J Child Adolesc Psychopharmacol, 15(6):986-995.

Thompson, D. A., Welle, S. L., Lilavivat, U., Penicaud, L., and Campbell, R. G. (1982). Opiate receptor blockade in man reduces 2-deoxy-D-glucose-induced food intake but not hunger, thirst, and hypothermia. Life Sci, 31(9):847-852.

Tonra, J. R., Ono, M., Liu, X., Garcia, K., Jackson, C., Yancopoulos, G. D., Wiegand, S. J., and Wong, V. (1999). Brain-derived neurotrophic factor improves blood glucose control and alleviates fasting hyperglycemia in C57BLKS-Lepr(db)/lepr(db) mice. Diabetes, 48(3):588-594.

Torrey, E. F. (2002). Studies of individuals with schizophrenia never treated with antipsychotic medications: a review. Schizophr Res, 58(2-3):101-115.

Trenchard, E., and Silverstone, T. (1983). Naloxone reduces the food intake of normal human volunteers. Appetite, 4(1):43-50.

Ventriglia, M., Bocchio Chiavetto, L., Bonvicini, C., Tura, G. B., Bignotti, S., Racagni, G., and Gennarelli, M. (2002). Allelic variation in the human prodynorphin gene promoter and schizophrenia. Neuropsychobiology, 46(1):17-21.

Volavka, J., Davis, L. G., and Ehrlich, Y. H. (1979). Endorphins, dopamine, and schizophrenia. Schizophr Bull, 5(2):227-239.

Wang G J, Volkow N D, Logan J, Pappas N R, Wong C T, Zhu W, Netusil N, Fowler J S. Brain dopamine and obesity. Lancet. 2001; 357(9253):354-7.

Weickert, C. S., Hyde, T. M., Lipska, B. K., Herman, M. M., Weinberger, D. R., and Kleinman, J. E. (2003). Reduced brain-derived neurotrophic factor in prefrontal cortex of patients with schizophrenia. Mol Psychiatry, 8(6):592-610.

Weizman, T., Pick, C. G., Backer, M. M., Rigai, T., Bloch, M., and Schreiber, S. (2003). The antinociceptive effect of amisulpride in mice is mediated through opioid mechanisms. Eur J Pharmacol, 478(2-3): 155-159.

Welch, E. B., and Thompson, D. F. (1994). Opiate antagonists for the treatment of schizophrenia. J Clin Pharm Ther, 19(5):279-283.

Wiegant, V. M., Ronken, E., Kovacs, G., and De Wied, D. (1992). Endorphins and schizophrenia. Prog Brain Res, 93:433-453.

Will, M. J., Franzblau, E. B., and Kelley, A. E. (2003). Nucleus accumbens mu-opioids regulate intake of a high-fat diet via activation of a distributed brain network. J Neurosci, 23(7):2882-2888.

Willenbring, M. L., Morley, J. E., Krahn, D. D., Carlson, G. A., Levine, A. S., and Shafer, R. B. (1989). Psychoneuroendocrine effects of methadone maintenance. Psychoneuroendocrinology, 14(5):371-391.

Xu, B., Goulding, E. H., Zang, K., Cepoi, D., Cone, R. D., Jones, K. R., Tecott, L. H., and Reichardt, L. F. (2003). Brain-derived neurotrophic factor regulates energy balance downstream of melanocortin-4 receptor. Nat Neurosci, 6(7):736-742.

Yeomans, M. R., and Gray, R. W. (1996). Selective effects of naltrexone on food pleasantness and intake. Physiol Behav, 60(2):439-446.

Yeomans, M. R., and Gray, R. W. (1997). Effects of naltrexone on food intake and changes in subjective appetite during eating: evidence for opioid involvement in the appetizer effect. Physiol Behav, 62(1):15-21.

Yeomans, M. R., and Gray, R. W. (2002). Opioid peptides and the control of human ingestive behaviour. Neurosci Biobehav Rev, 26(6):713-728.

Yeomans, M. R., and Wright, P. (1991). Lower pleasantness of palatable foods in nalmefenetreated human volunteers. Appetite, 16(3):249.-259.

Yeomans, M. R., Wright, P., Macleod, H. A., and Critchley, J. A. (1990). Effects of nalmefene on feeding in humans. Dissociation of hunger and palatability. Psychopharmacology (Berl), 100(3):426-432.

Zador, D., Lyons Wall, P. M., and Webster, I. (1996). High sugar intake in a group of women on methadone maintenance in south western Sydney, Australia. Addiction, 91(7):1053-1061.

Zukin, R. S., Sugarman, J. R., Fitz-Syage, M. L., Gardner, E. L., Zukin, S. R., and Gintzler, A. R. (1982). Naltrexone-induced opiate receptor supersensitivity. Brain Res, 245(2): 285-292.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the appended claims.

What is claimed is:

1. A method of treating a sequela of weight gain in a human subject treated with a second generation antipsychotic agent (SGA), said method comprising administering an opioid receptor antagonist to said subject suffering from said sequela in an amount sufficient to treat said sequela, wherein the SGA is olanzapine, the opioid receptor antagonist is naltrexone, and the subject is not suffering from co-morbid substance abuse or dependence.

2. The method of claim 1, wherein said method further comprises the step of diagnosing said sequela in said subject prior to said administering.

3. The method of claim 1, wherein said subject is suffering from a psychiatric disorder.

4. The method of claim 3, wherein said psychiatric disorder is selected from the group consisting of schizophrenia, psychosis, schizoaffective disorder, and bipolar disorder.

5. The method of claim 1, wherein said sequela is selected from the group consisting of weight gain, obesity, metabolic syndrome, insulin resistance, abdominal adiposity, impaired, glucose tolerance, dyslipidaemia, hypercholesterolemia, diabetes, and hypertension.

6. The method of claim 1, wherein said opioid receptor antagonist is administered at less than 10 mg per day.

7. The method of claim 6, wherein said opioid receptor antagonist is administered at less than 1 mg, 0.1 mg, 0.01 mg, or 0.001 mg per day.

8. The method of claim 1, wherein the ratio of opioid receptor antagonist to SGA is at most 1:1,000.

9. The method of claim 1, wherein said subject has a BMI of greater than or equal to 30 kg/m$^2$ or greater than or equal to 27 kg/m$^2$ and at least one symptom of metabolic syndrome.

10. The method of claim 1, wherein said subject has a BMI of less than 30 kg/m$^2$ and said subject has increased pain sensitivity.

11. The method of claim 1, wherein said treating results in a reduction in waist/hip ratio or fat body mass.

12. A method of treating a psychiatric disorder, said method comprising administering a second generation antipsychotic agent (SGA) and an opioid receptor antagonist to a human subject suffering from said psychiatric disorder in an amount sufficient to treat said psychiatric disorder, wherein said administration results in a reduction of a sequela of weight gain, wherein the SGA is olanzapine, the opioid receptor antagonist is naltrexone, and the subject is not suffering from co-morbid substance abuse or dependence.

13. The method of claim 12, wherein said psychiatric disorder is selected from the group consisting of schizophrenia, psychosis, schizoaffective disorder, and bipolar disorder.

14. The method of claim 12, wherein said treating results in a reduction in waist/hip ratio or fat body mass.

15. A method of treating a sequela of weight gain in a human subject suffering from a psychiatric disorder, said method comprising administering a second generation antipsychotic agent (SGA) and an opioid receptor antagonist to said subject in an amount sufficient to treat said sequela, wherein the SGA is olanzapine, the opioid receptor antagonist is naltrexone, and the subject is not suffering from co-morbid substance abuse or dependence.

16. The method of claim 15, wherein said psychiatric disorder is selected from the group consisting of schizophrenia, psychosis, schizoaffective disorder, and bipolar disorder.

17. The method of claim 15, wherein said treating results in a reduction in waist/hip ratio or fat body mass.

* * * * *

UNITED STATES PATENT AND TRADEMARK OFFICE
CERTIFICATE OF CORRECTION

PATENT NO. : 8,551,986 B2  
APPLICATION NO. : 12/096428  
DATED : October 8, 2013  
INVENTOR(S) : Igor Elman et al.

Page 1 of 1

It is certified that error appears in the above-identified patent and that said Letters Patent is hereby corrected as shown below:

In the Claims

Column 20, Line 13, Claim 12, replace "subiect" with --subject--.

Signed and Sealed this  
Eighth Day of April, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,551,986 B2 | Page 1 of 1 |
| APPLICATION NO. | : 12/096428 | |
| DATED | : October 8, 2013 | |
| INVENTOR(S) | : Elman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1103 days.

Signed and Sealed this
Tenth Day of March, 2015

Michelle K. Lee
*Deputy Director of the United States Patent and Trademark Office*